United States Patent [19]

Ou

[11] Patent Number: 5,208,367
[45] Date of Patent: May 4, 1993

[54] PROCESS FOR RECOVERY OF VINYL ACETATE

[75] Inventor: John D. Ou, Houston, Tex.

[73] Assignee: Exxon Chemical Patents Inc., Linden, N.J.

[21] Appl. No.: 809,453

[22] Filed: Dec. 17, 1991

[51] Int. Cl.$^5$ .................. B01D 3/36; C07C 67/54
[52] U.S. Cl. .................. 560/248; 203/96; 203/97
[58] Field of Search .............. 560/248; 203/39, 53, 203/71, 51, 65, 96, 97

[56] References Cited

U.S. PATENT DOCUMENTS

| | | | |
|---|---|---|---|
| 2,349,807 | 5/1944 | Benedict | 260/499 |
| 2,350,087 | 5/1944 | Benedict | 260/499 |
| 2,724,717 | 11/1955 | Hibshman | 260/450 |
| 3,182,006 | 5/1965 | Fruhwirth | 202/42 |
| 3,458,406 | 7/1969 | Fisher et al. | 203/44 |
| 3,679,764 | 7/1972 | Hinton et al. | 260/680 E |
| 3,691,021 | 9/1972 | Feldman et al. | 203/65 |
| 3,692,636 | 9/1972 | Huguet | 203/71 |
| 3,736,236 | 5/1973 | Di Fiore et al. | 203/39 |
| 3,738,915 | 6/1973 | Di Fiore et al. | 203/39 |
| 4,543,164 | 9/1985 | Berg et al. | 560/248 X |
| 4,544,453 | 10/1985 | Gupta | 203/44 |
| 4,569,726 | 2/1986 | Berg et al. | 560/248 X |
| 4,597,834 | 7/1986 | Berg et al. | 203/51 |
| 4,666,560 | 5/1987 | Berg et al. | 203/65 X |
| 4,897,161 | 1/1990 | Berg et al. | 203/51 |
| 4,925,533 | 5/1990 | Berg | 203/51 |
| 4,934,519 | 6/1990 | Wolf et al. | 203/96 |

Primary Examiner—Arthur C. Prescott
Attorney, Agent, or Firm—Linda K. Russell

[57] ABSTRACT

A two-step extraction method for the separation of vinyl acetate from a liquid mixture containing oxygenated compounds, paraffins and olefins, vinyl acetate, water, heavy oils, and other impurities, such as an antioxidant, is provided. The first step of the process extracts vinyl acetate and oxygenated compounds from the liquid mixture with a water wash. The paraffins, olefins, and heavy oils are insoluble in the water wash and are recovered as a waste stream from the wash. In a second step the vinyl acetate-rich water is distilled in a steam stripper column. Water is collected as the bottoms from the column and the overhead vapors are cooled by a condenser and collected in a separator tank. The separator tank liquids separate into an aqueous phase and a vinyl acetate phase. The aqueous phase is a waste stream. The vinyl acetate phase is recovered and may be used as a feedstock for polymerization or copolymerization reactions.

17 Claims, 3 Drawing Sheets

PROCESS FOR RECOVERY OF VINYL ACETATE

BACKGROUND OF THE INVENTION

This invention relates to a process for recovery of vinyl acetate from a liquid mixture of vinyl acetate, paraffins and other impurities, and more particularly, relates to a two-step extraction process for the recovery of vinyl acetate from a liquid mixture of vinyl acetate, paraffins and other impurities.

Vinyl acetate may be manufactured by the oxidative addition of acetic acid to ethylene in the presence of a palladium catalyst. In general, either liquid phase or vapor phase processes are used commercially. In the liquid phase process, a mixture of ethylene and oxygen are fed into a single stage reactor which contains acetic acid, water and the catalyst. The products, i.e., vinyl acetate and acetaldehyde are separated from the exiting gas stream in a series of distillation columns. In the vapor phase process, a catalytic process is also used for vinyl acetate production, but is based on acetic acid addition to gaseous acetylene.

These vinyl acetate monomers are recovered and then used as feedstocks for various polymerization or copolymerization reactions to make polyvinyl acetate or other copolymers. The vinyl acetate monomer is usually stored in tanks before being used and has anti-oxidants added to it, in low percentages by weight, to prevent self-polymerization reactions in the storage tanks.

In more detail, one conventional copolymerization reaction involves copolymerizing ethylene with vinyl acetate in a reactor. The desired product is a polymer and the process is exothermic so that a diluent, usually iso-octane or some other paraffin, is used to control the amount of material entering the polymerization reaction and thereby control the heat generated in the polymerization reactor. The process also produces various by-products such as oxygenates that may be alcohols, ketones, or aldehydes.

The liquid mixture from this reaction includes the anti-oxidants, byproduct contaminants, diluents, unreacted components (ethylene and vinyl acetate), as well as the polymer product. The polymer product is extracted by appropriate means and then any unreacted ethylene may be easily removed from the liquid mixture by a single distillation step. This leaves a liquid waste stream of vinyl acetate, diluents, oxygenates, and anti-oxidants. This waste stream is then diverted to waste storage tanks which may have previously contained almost anything, such as, for example, paraffins and/or olefins and heavy oils containing olefins and/or aromatics. When removed from these tanks, the waste stream will contain small amounts of such prior tank contents as additional contaminants or impurities.

Thus, such vinyl acetate polymerization or copolymerization processes may result in a liquid mixture of vinyl acetate and other impurities, such as paraffins, which form azeotropes with vinyl acetate and so may not be removed by conventional extractive distillation steps, as well as the other types of impurities noted before. As noted before, in addition to paraffins and/or olefins which may be present, such liquid mixtures may also include heavy oils which may be olefins and/or aromatics (with "heavy" meaning a boiling point higher than the boiling point of vinyl acetate). Other types of impurities may be water, anti-oxidants, and/or acetaldehyde (or other oxygenated compounds, such as methanol and acetone), or other alcohols, ketones, or aldehydes. It is conventional practice in the plastics industry to discard or burn such liquid waste stream mixtures of vinyl acetate and other impurities. However, in order to recover more vinyl acetate and to reduce the amount of waste material that must be reprocessed or discharged, a process for the recovery of vinyl acetate from such waste streams is desirable.

These and other limitations and disadvantages of the prior art are overcome by the present invention, however, and improved methods are provided for the separation of vinyl acetate from liquid mixtures containing oxygenated compounds, paraffins, vinyl acetate, water, anti-oxidants, and other contaminants.

SUMMARY OF THE INVENTION

In a preferred embodiment of the present invention, a method for the separation of vinyl acetate from a liquid mixture containing oxygenated compounds, paraffins, olefins, aromatics, vinyl acetate, water and other impurities is provided. More particularly, a two-step extraction process is provided for extracting vinyl acetate from such liquid mixtures. The first extractive step of the process is to initially extract vinyl acetate and the oxygenated compounds from the mixture by a water wash. The paraffins, olefins and other heavy oils are insoluble in the water wash and are recovered as a waste stream from the wash. In a second extractive step, the vinyl acetate-rich water is distilled in a steam stripper column. Water is collected as the bottoms from the column and the overhead vapors or gases are cooled by a condenser and collected in a separator tank. The liquids in the separator tank separate into an aqueous phase and a vinyl acetate phase. The aqueous phase is discharged as a waste stream, while the vinyl acetate phase is recovered and then may be used as a vinyl acetate feedstock for polymerization reactions. Preferably the stripper column is operated at a partial vacuum to reduce the boiling point of the vinyl acetate and thereby reduce its reactivity. Preferably steam supplies the heat for operating the stripper column.

It is an object of the present invention to provide a method for the separation of vinyl acetate from liquid mixtures containing oxygenated compounds, paraffins and olefins, vinyl acetate, water and other impurities, such as anti-oxidants and heavy oils.

It is an object of the present invention to provide a method for the separation of vinyl acetate from liquid mixtures containing alcohols, acetone and/or acetaldehyde (or other ketones or aldehydes), paraffins and olefins, vinyl acetate, water and other impurities, such as anti-oxidants and heavy oils.

It is also an object of the present invention to provide a method for the recovery of vinyl acetate from a waste stream containing oxygenated compounds, paraffins and olefins, vinyl acetate, water and other impurities, such as anti-oxidants and heavy oils.

It is also an object of the present invention to provide a method for the recovery of vinyl acetate from a waste stream containing alcohols, acetone and/or acetaldehyde (or other ketones or aldehydes), paraffins and olefins, vinyl acetate, water and other impurities, such as anti-oxidants and heavy oils.

Accordingly, these and other objects and advantages of the present invention will become apparent from the following detailed description, wherein reference is made to the figures in the accompanying drawings.

IN THE DRAWINGS

DETAILED DESCRIPTION

Figure 1:
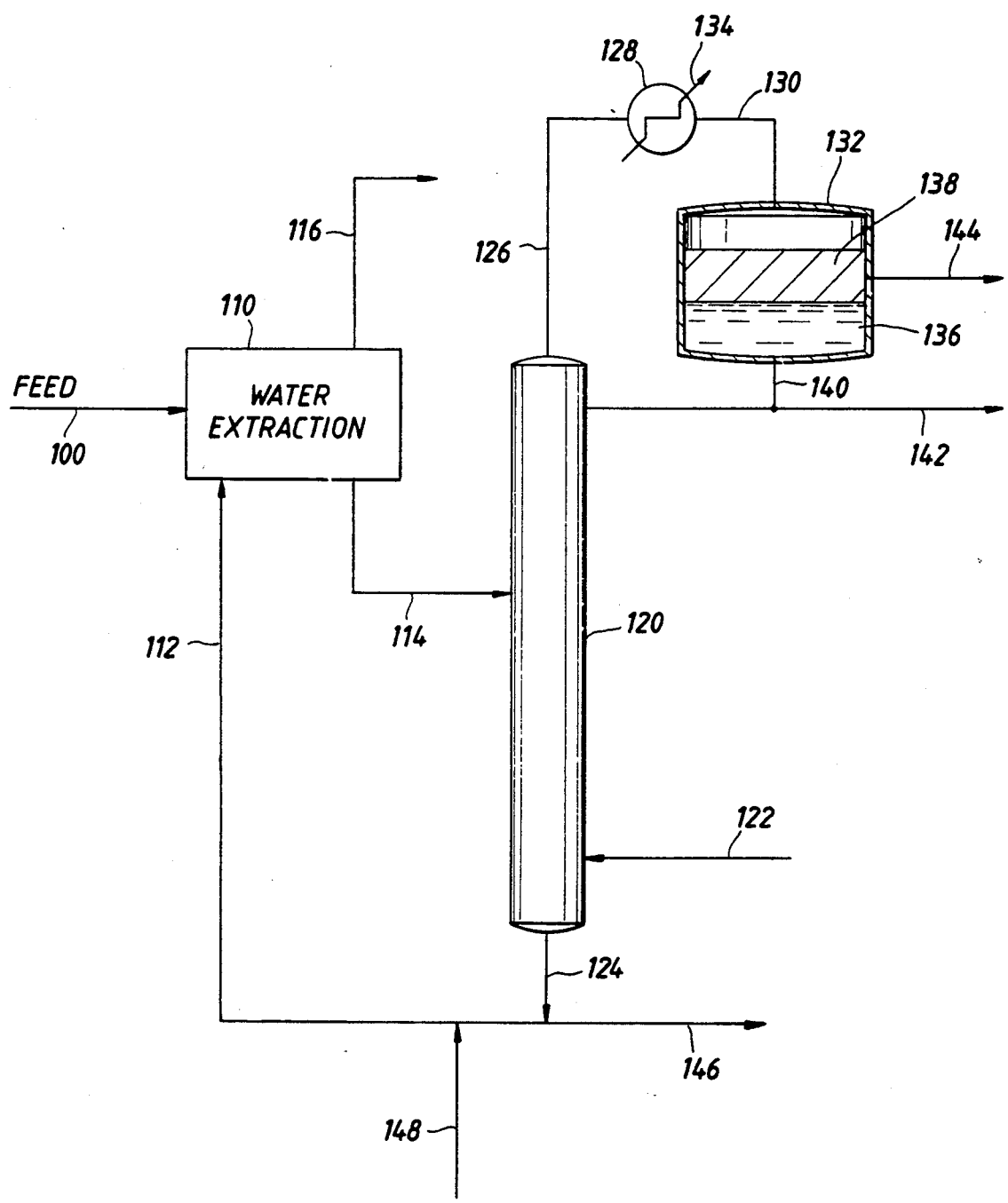
FIG. 1 is a simplified flow diagram illustrating a method of the present invention for the recovery of vinyl acetate from a liquid stream containing vinyl acetate and other impurities.

Referring now to FIG. 1 there may be seen a simplified flow diagram of the method of the present invention for the recovery of vinyl acetate from a liquid mixture containing vinyl acetate and other impurities. More particularly, continuing to refer to FIG. 1, there may be seen a liquid feed stream 100 to a first water extraction step 110. This liquid feed stream 100 may be from various processes and is preferably a discharge or waste stream from a vinyl acetate polymerization or copolymerization reaction. This mixture 100 may contain approximately 80-90% vinyl acetate and various paraffins, such as iso-octane and/or hexane. More particularly, the iso-octane may vary between about 3 to about 22% and the hexane may vary between about 0 to about 6%. The mixture 100 may also include water and anti-oxidants, as well as small amounts of other impurities, such as other paraffins and/or olefins and heavy oils containing olefins and/or aromatics. In addition, oxygenated compounds such as methanol, acetone, acetaldehyde, or other types of alcohols, ketones, and aldehydes may also be found in this same liquid mixture 100 in a few percents, i.e., from about 1 to about 5%, either individually or in combination.

Initially the liquid feed mixture 100 is fed to a first water extraction step 110 where excess water 112 is injected into the liquid mixture 100 and a vinyl acetate-rich water stream 114 is recovered. Sufficient water 112 must be injected into the feed mixture 100 to extract the vinyl acetate without forming a water-rich stream saturated with vinyl acetate (which may result in some vinyl acetate not being extracted). In addition, a vinyl acetate-depleted waste stream 116 is recovered which contains essentially all of the hydrocarbons, such as paraffins and olefins, and heavy oils, as well as any water insoluble antioxidants. This first step 110 employs the concept that vinyl acetate is soluble in water as are the oxygenated compounds, while hydrocarbons, such as hexane and iso-octane and other paraffins and olefins, heavy oils, and most antioxidants, are essentially insoluble in water.

Thus, it is possible to use water having a boiling point significantly higher than the vinyl acetate, to dilute and then extract the vinyl acetate from the liquid feed mixture. Alternatively, other polar solvents may be employed in combination with or in place of water. That is, the vinyl acetate-depleted waste stream 116 is approximately 80% paraffins, olefins, and heavy oils, and about 20% vinyl acetate. The vinyl acetate-depleted stream 116 contains about 98% of the paraffins, olefins, heavy oils, and antioxidants present in the initial feed mixture 100 and about 5% of the vinyl acetate in the initial feed mixture 100. The vinyl acetate-rich water stream 114 constitutes approximately 95% of the vinyl acetate from the initial feed mixture 100 and other water soluble impurities. This water extraction step 110 may be conducted at temperatures ranging from about 10° C. to about 100° C. and from pressures ranging from about 15 psia to about 1,000 psia.

The vinyl acetate-rich water stream 114 is then fed to a steam stripper column 120. The steam 122 supplied to the stripper column 120 is preferably the only heat source for the column. The steam 122 may be supplied from any convenient source. The column 120 may be operated at 40° C. to about 200° C. and about 5 psia to about 500 psia. Condensed steam or water 124 is recovered at the bottom of the stripper column 120, while the vapors 126 which contain steam, vinyl acetate and other oxygenated compounds are recovered at the top of the stripper column 120.

These vapors 126 are then condensed by a condenser 128 and the condensed vapors 130 supplied to a separator tank 132. The condenser 128 is supplied with cooling water 134 and may operate at about 25° C. to about 40° C. and from about 5 psia to about 500 psia. The separator tank 132 allows the condensed vapors 130 to separate into an aqueous phase 136 and a vinyl acetate phase 138. The separator tank 132 is operated at about 25° C. to about 40° C. and from about 5 psia to about 500 psia.

The aqueous phase 136 contains some portion of the oxygenated compounds. The higher the water to vinyl acetate ratio in the vapors 126 the more the oxygenates will be partitioned into the water phase 136 and the purer the vinyl acetate phase 138 will be. In general this aqueous phase 136 will contain approximately 40% of the oxygenates in solution. The remainder of the oxygenates will be contained in the vinyl acetate phase 138. This vinyl acetate phase 138 will consist of approximately 98% or more vinyl acetate and approximately 1½% of the oxygenates and any water soluble antioxidants.

The separator tank 132 is a conventional separator tank with a baffle wall to create a chamber for the collection of the condensed vapors 130 from the steam stripper column 120 which allows the lighter, vinyl acetate phase 138 to flow over the baffle and be recovered; the aqueous phase 136 is the bottom portion of the two phases behind the baffle area. This allows a pipe 140 at the bottom of the baffle area to discharge the aqueous phase 136 as a waste water stream 142. A separate connection 144 on the other side of the baffle allows for recovery of the vinyl acetate phase 138. The concentration of vinyl acetate in the vinyl acetate phase 138 is sufficiently pure to allow this recovered vinyl acetate stream to serve as the feedstock for a polymerization or copolymerization reaction that results in polymers and copolymers of sufficient purity for use in packaging for food and/or foodstuffs.

Preferably the steam stripper column 120 is run at a partial vacuum to reduce the boiling point of the vinyl acetate. As is well known, the reactivity of vinyl acetate is based upon its temperature, and accordingly reducing the boiling point reduces its reactivity. This in turn reduces the corrosion wear on the column and the downstream portions of this process by virtue of the reduced reactivity of the vinyl acetate.

A water purge line 146 may be employed to remove water for storage or disposal. Similarly, a water makeup line 148 may be employed to add water to the water injection line 112 for the water extraction step 110, if an insufficient amount of water 124 is recovered from the column 120.

Although other polar solvents may be employed in the process of the present invention, such solvents must be approved for the final end use (such as packaging for food products) of the polymers employing the recovered vinyl acetate.

The present invention will be further described by the following examples, which illustrate methods and apparatus in accordance with the present invention. The examples are provided for illustration and are not intended to limit the scope of the present invention in any way to any of the specific parameters set forth therein.

EXAMPLE 1

The first example is representative of a portion of the process of the present invention. A simple laboratory extraction experiment verified the concept of the first step of water extraction of vinyl acetate, in a batch mode. One gram of a 50 weight % vinyl acetate with a 50 weight % hexane mixture was allowed to contact 16.4 grams of water at room temperature in a sealed bottle. The liquids were then stirred for thirty minutes. After equilibration, a gas chromatograph analysis showed that organic compounds in the water phase contained 99.45% vinyl acetate and 0.55% hexane.

EXAMPLE 2

Figure 2:
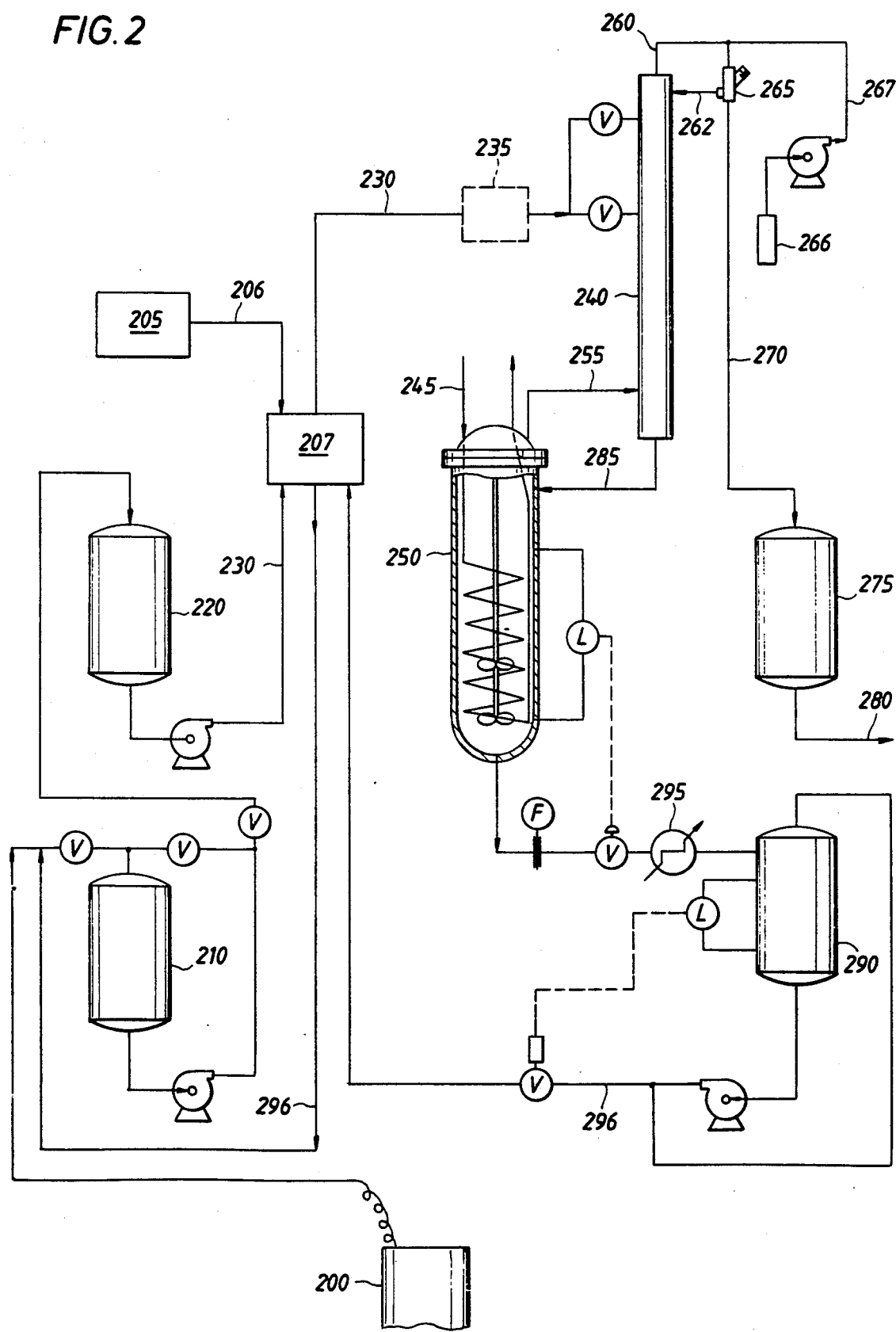
FIG. 2 is a simplified flow diagram illustrating a pilot plant configuration employed to simulate a method of the present invention.

The second example is based upon a pilot plant (depicted in FIG. 2) run to demonstrate water extraction and stripping of vinyl acetate from a waste stream. The feedstock (in a drum 200) was a mixture of approximately 75% vinyl acetate (78%), 20% iso-octane, and 5% miscellaneous oxygenates. The vinyl acetate was first extracted by water in a batch mode. That is, a portion of the feedstock (from drum 200) was well mixed with water in a first tank 210 to provide an approximately 2% by weight vinyl acetate in water solution, and extract the vinyl acetate from the hydrocarbon portion of the feedstock. (Note that an approximately 2% by weight vinyl acetate concentration in water is an approximately saturated water solution.)

As noted later herein, multiple batch extractions were employed to avoid problems with a saturated water mixture not extracting all the vinyl acetate in the feedstock. The mixture of feedstock and water in tank 210 was then allowed to separate into a water phase and hydrocarbon phase. The water phase (was essentially saturated with vinyl acetate) was pumped to a second tank 220 and was then used as the feed 230 for a second extraction step employing a column 240.

The vinyl acetate/water mixture from the second tank 220 was continuously fed (62 lbs/hr) to the middle of a 6″ diameter, 20 foot, packed, twenty stage distillation column 240 for a continuous separation of additional impurities from vinyl acetate, at 15 psig. Steam (150 psi) 245 was supplied to a reboiler 250 which provided hot (250° F.) water 255 (as a heat source) to the distillation column 240 (which was also fed the vinyl acetate/water mixture 230 from the second tank 220). A very small overhead vapor phase 260 at about 65° C. (approximately 4% of the feed rate) was passed from the column 240 to an overhead condenser 265, where the vapor phase 260 was condensed. The condensate 270 was stored in an intermediate tank 275 and then transferred (via line 280) to a final separation tank (not depicted) where separate vinyl acetate and water phases were allowed to form.

The water 285 from the bottoms of the column 240 were recirculated to the reboiler 250. A major portion of the bottoms water in the reboiler 250 was passed to a separate storage tank 290, after being cooled via a heat exchanger 295, and then was used as recycle water 296 or to perform additional batch extractions of vinyl acetate from the feedstock in the first tank 210. Batch extractions were repeated until the vinyl acetate was completely extracted from the hydrocarbons in the feedstock. A makeup water tank 205 and supply line 206 supplied makeup water to a valve manifold 207 (that was aligned to provide the appropriate flow paths).

Operational procedures were changed as various equipment problems were discovered in an attempt to stabilize operations. A feed pre-heater (steam heated) 235 (depicted in dashed lines) was added a few days after the pilot plant run was started to attempt to compensate for steam 245 flow rate control problems.

The distillation column 240 was not designed for continuous extraction, but the pilot plant runs crudely simulated a method of the present invention. Although the column's condenser 265 was not designed for two phases, it was employed in the pilot plant runs to condense two phases. Variables tested during the run included the overhead 260 phase ratio and the need for column reflux 262. Difficulties were experienced in adjusting reflux 262 to the column 240 and control of the overhead 260 phase ratio proved to be very difficult. A column having the correct design would make such operations very easy to control and adjust. Further, although initially thought unnecessary, hydroquinone 266 (0.5% hydroquinone in water) was injected 267 into the column overhead condenser 265 (to prevent internal polymerization) at the rate of 1.2 cc/min.

Even with all the equipment problems, the results demonstrated the operability of the methods of the present invention. High purity vinyl acetate may be produced and recovered using the extraction/stripping configuration of the pilot plant. Even with no reflux 262, vinyl acetate was completely recovered from the water. Increasing the overhead 260 water to vinyl acetate ratio increases vinyl acetate purity (i.e., less oxygenates are in the vinyl acetate) but decreases the amount recovered.

Once the feed pre-heater 235 was added, the average percentage of vinyl acetate in the vinyl acetate phase from the overhead condensate 270 during reasonably steady state continuous operation over a period of about 6 days was at least 98.75% and the average percentages of acetaldehyde, acetone (and other ketones), ethyl acetate, alcohols, and iso-octane were less than about 0.4, 0.13, 0.10, 0.13 and 0.28, respectively. The average percentage of vinyl acetate in the water phase was less than 2.62 and the average percentages of acetaldehyde, ketones, acetic acid and alcohols in the water phase were less than 0.52, 0.05, 0.04, and 0.03, respectively.

EXAMPLE 3

A third example illustrates a continuous extraction step. A portion of the equipment employed for the pilot plant was employed to simulate continuous extraction of vinyl acetate from the feedstock with water. A metered water stream (400 lbs/hr) and a much smaller metered feedstock stream of Example 2 (10 lbs/hr) were combined ahead of a static mixer. Samples were taken downstream of the mixer and the water analyzed for vinyl acetate. The results demonstrated that vinyl acetate may be extracted from hydrocarbons by water with a satisfactory recovery. The vinyl acetate concentration in the water was near saturation (about 1.8%) and analysis of the hydrocarbons showed approximately 93% recovery for the extraction of the vinyl acetate.

Figure 3:
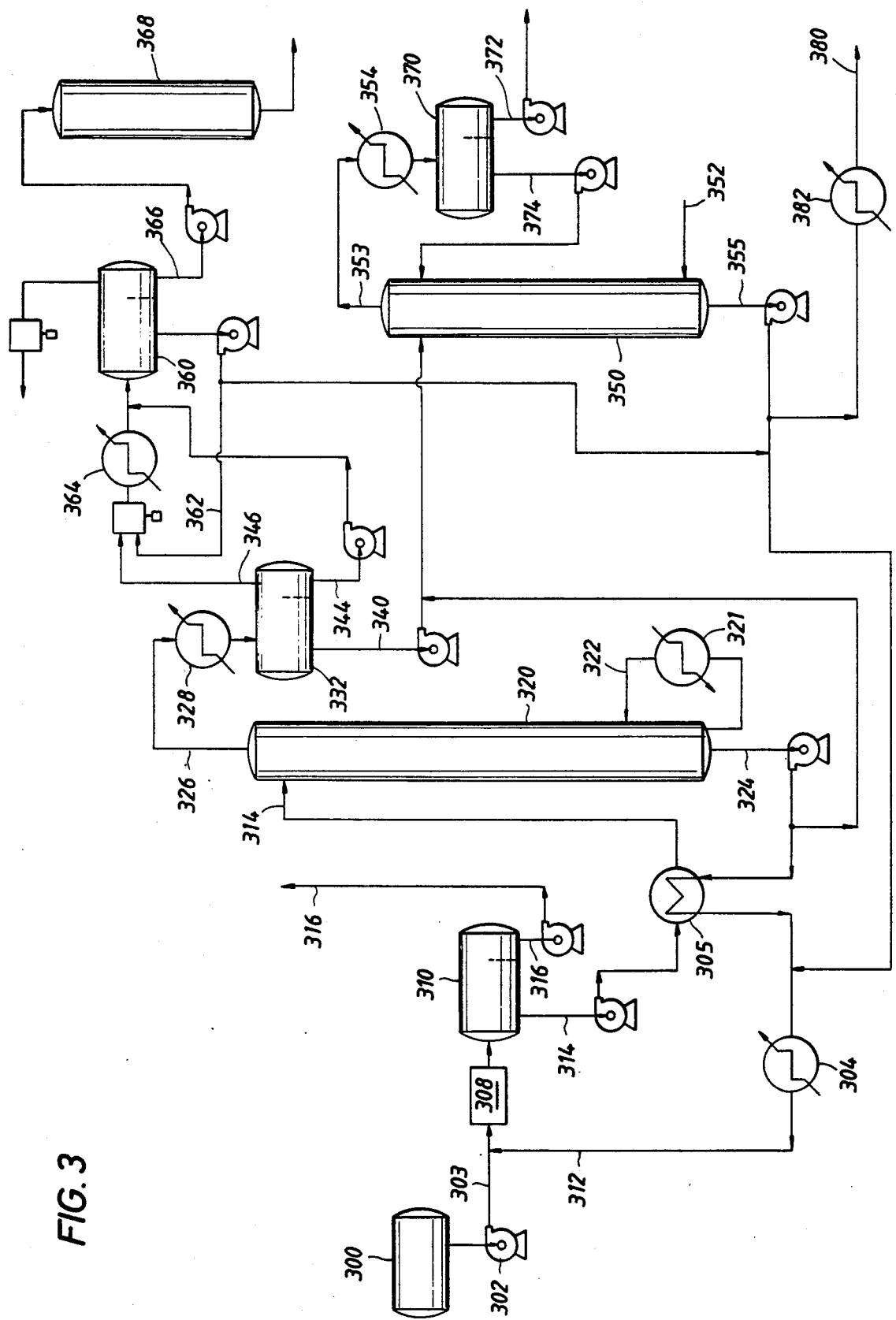
FIG. 3 is a simplified flow diagram of a method of the present invention suitable when no waste water cleanup facilities are available.

Referring now to FIG. 3, there may be seen a simplified flow diagram for recovery of vinyl acetate from a waste mixture when no waste water treatment facilities are available. Again there is an initial water extraction step 310 followed by steam stripping of the vinyl acetate/water mixture as noted in FIG. 1. More particularly, feedstock from tank 300 is pumped via pump 302 and line 303, into a mixer 308, where it is mixed with water from line 312. This mixture is passed into settling tank 310 where a vinyl acetate-rich phase is removed, via line 314, and pumped to a first steam stripper column 320. A vinyl acetate-depleted phase is removed via line 316. Steam 322 (from a boiler 321, or other source) supplied to the column 320 vaporizes the vinyl acetate-rich phase. The water 324 from the column's bottoms may be pumped through a heat exchanger 305 to preheat the feed 314 to the first column 320 before being cooled (by heat exchanger 304) and mixed as inlet water 312 with the feedstock 303.

The overhead vapors 326 are condensed in condenser 328 and supplied to a separator tank 332. A recovered waste water phase 340 is supplied to a second steam stripper column 350 supplied by steam 352 from an appropriate source of steam. A recovered vinyl acetate phase 344 is supplied to a second separator tank 360. The vapors 346 from the first separator tank 332 are mixed with a recycle stream 362 from the second separator tank 360, cooled via condenser/heat exchanger 364, and injected into the second separator tank 36 after mixing with the discharged vinyl acetate phase 344 from the first separator tank. The vapors from the second separator tank 360 may be burned or "flared." The vinyl acetate phase 366 from the second separator tank is "dried" by a drier and then used as vinyl acetate feed stock.

The waste water phase 340 is vaporized in the second steam stripper column 350 and the vapors 353 condensed by condenser 354 before being passed into a separator tank 370. An organics phase 372 is separated from an aqueous phase 374, which is reinjected into the second column 350. Appropriately cleaned (organics removed) water 355 from the bottom of the second column 350 may be employed as a water source or purged to a sewer system 380 (via a heat exchanger 382). Again, either or both columns may be operated at a partial vacuum.

A second steam stripping column has been added to remove organics from the water phase of the first column before discharging the water to a conventional commercial sewer. This second steam stripping may be necessary when a manufacturing facility lacks appropriate waste water treatment facilities.

Thus, it may be seen that the present invention provides methods for the separation of vinyl acetate from liquid mixtures containing vinyl acetate and other contaminants.

Many other variations and modifications may be made in the apparatus and methods hereinbefore described, by those having experience in this technology, without departing from the concept of the present invention. Accordingly, it should be clearly understood that the apparatus and methods depicted in the accompanying drawings and referred to in the foregoing description are illustrative only and are not intended as limitations on the scope of the invention.

What is claimed is:

1. A method for the separation of vinyl acetate from liquid mixtures containing oxygenated compounds, paraffins and/or olefins, vinyl acetate, water, heavy oils, and antioxidants, comprising:
   extracting vinyl acetate and other polar compounds in said liquid mixtures from non-polar compounds in said liquid mixtures with water to provide a vinyl acetate-rich water extract,
   distilling the vinyl acetate-rich water extract with steam,
   recovering and condensing vapors from said distilling step, and
   separating said condensed vapors into a vinyl acetate phase and an aqueous phase.

2. A method as described in claim 1, wherein said extracting step comprises
   mixing said liquid mixtures with a sufficient amount of water to form a non-saturated solution of vinyl acetate in said water,
   separating a polar stream from a non-polar stream, discarding said non-polar stream, and
   providing said polar stream to said distilling step as said vinyl acetate-rich extract.

3. A method as described in claim 1, wherein said extracting step is conducted at a temperature of about 10° C. to about 100° C.

4. A method as described in claim 1, wherein said extracting step is conducted at a pressure of about 15 psia to about 1,000 psia.

5. A method as described in claim 1, wherein said distilling step is conducted at a temperature of about 40° C. to about 200° C.

6. A method as described in claim 1, wherein said distilling step is conducted at a pressure of about 5 psia to about 500 psia.

7. A method as described in claim 1, wherein said recovering and condensing step further comprises, adding a self-polymerizing inhibiting agent.

8. A method as described in claim 1, further comprising:
   distilling said separated aqueous phase with steam,
   recovering and condensing vapors from said distilled aqueous phase, and
   separating said condensed vapors into an aqueous phase and an organics phase.

9. A method as described in claim 8, further comprising, adding said organics phase to said vinyl acetate phase.

10. A method for the recovery of vinyl acetate from liquid mixtures containing oxygenated compounds, paraffins and/or olefins, vinyl acetate, water, heavy oils and anti-oxidants, comprising:
    contacting said liquid mixtures with an excess of water to provide a vinyl acetate-rich water phase,
    distilling said vinyl acetate-rich water phase with steam,
    recovering vapors from said distilling step,
    condensing said recovered vapors,
    separating said condensed vapors into an aqueous phase and a vinyl acetate phase, and
    recovering said vinyl acetate phase.

11. A method as described in claim 10, further comprising:
    distilling said separated aqueous phase with steam,
    recovering vapors from said distilled aqueous phase, condensing said recovered vapors, and separating said condensed vapors into an aqueous phase and an organics phase.

12. A method as described in claim, 11, further comprising, adding said organics phase to said vinyl acetate phase.

13. A method as described in claim 10, wherein said extracting step is conducted at a temperature of about 10° C. to about 100° C.

14. A method as described in claim 10, wherein said extracting step is conducted at a pressure of about 15 psia to about 1,000 psia.

15. A method as described in claim 10, wherein said distilling step is conducted at a temperature of about 40° C. to about 200° C.

16. A method as described in claim 10, wherein said distilling step is conducted at a pressure of about 5 psia to about 500 psia.

17. A method as described in claim 10, wherein said recovering and condensing step further comprises, adding a self-polymerizing inhibiting agent.

* * * * *